United States Patent [19]

Lacefield et al.

[11] Patent Number: 4,552,982

[45] Date of Patent: Nov. 12, 1985

[54] SYNTHESIS OF 9-CARBAMOYL-9-(3-AMINOPROPYL)FLUORENES

[75] Inventors: William B. Lacefield; William Pfeifer, both of Indianapolis, Ind.

[73] Assignee: Eli Lilly and Company, Indianapolis, Ind.

[21] Appl. No.: 519,166

[22] Filed: Aug. 1, 1983

[51] Int. Cl.$^4$ ............................................ C07C 103/28
[52] U.S. Cl. ................................... 564/164; 564/129; 564/415; 564/493
[58] Field of Search ................ 564/164, 415, 493, 129

[56] References Cited

U.S. PATENT DOCUMENTS

| | | | |
|---|---|---|---|
| 3,468,953 | 9/1969 | Besson et al. | 564/493 X |
| 4,197,313 | 4/1980 | Lacefield et al. | 424/304 |
| 4,277,471 | 7/1981 | Lacefield et al. | 564/164 X |
| 4,282,170 | 8/1981 | Lavagnino et al. | 260/465 D |
| 4,382,093 | 5/1983 | Lacefield et al. | 424/324 |
| 4,452,745 | 6/1984 | Lacefield et al. | 564/164 X |

FOREIGN PATENT DOCUMENTS

| | | | |
|---|---|---|---|
| 1124485 | 3/1962 | Fed. Rep. of Germany | 564/415 |
| 1164354 | 9/1969 | United Kingdom | 564/493 |

Primary Examiner—Thomas A. Waltz
Attorney, Agent, or Firm—Charles W. Ashbrook; Arthur R. Whale

[57] ABSTRACT

9-Carbamoyl-9-(2-cyanoethyl)fluorenes are converted to 9-carbamoyl-9-(3-aminopropyl)fluorenes by catalytic hydrogenation in the presence of a strong acid.

7 Claims, No Drawings

SYNTHESIS OF 9-CARBAMOYL-9-(3-AMINOPROPYL)FLUORENES

BACKGROUND OF THE INVENTION

A group of 9-aminoalkylfluorenes recently has been disclosed as having valuable antiarrhythmic activity; see U.S. Pat. Nos. 4,197,313 and 4,277,495. The 9-carbamoyl-9-aminoalkylfluorenes are among the most interesting compounds, and one compound within this group, namely 9-carbamoyl-9-(3-isopropylaminopropyl)fluorene, is now known generically as indecainide.

Lavagnino et al., in U.S. Pat. No. 4,282,170, disclose a process for preparing 9-carbamoyl-9-(3-aminopropyl)-fluorene, an intermediate in a synthesis of indecainide, which process comprises hydrogenation of 9-carbamoyl-9-(2-cyanoethyl)fluorene. The hydrogenation reaction is said to be best carried out in an acidic medium, most preferably in glacial acetic acid, although organic solvents such as ethanol can be employed if desired.

We have now discovered that the hydrogenation process described in U.S. Pat. No. 4,282,170 leads to formation of observable quantities of fluorene dimer and trimer by-products, compounds of the formulas

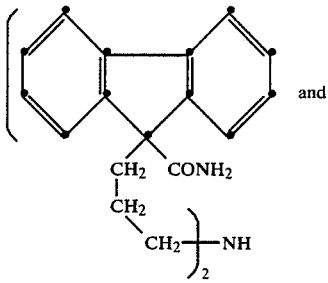

and

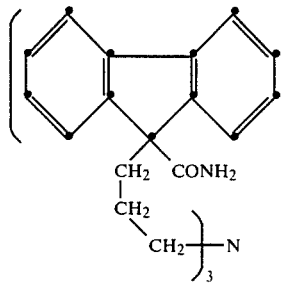

Removal of these by-products has proved extremely difficult, and in general they are carried through subsequent reactions and can be found in the final product.

An object of this invention is to provide an improvement in the process for hydrogenating 9-carbamoyl-9-(2-cyanoethyl)fluorene. The improvement provided by this invention results in reduced amounts of the aforementioned fluorene dimer and trimer by-products being produced, and thereby permits formation of a purer pharmaceutical agent.

SUMMARY OF THE INVENTION

This invention concerns an improvement in a process for converting a cyanoethylfluorene to an aminopropylfluorene. The invention more particularly provides, in the process for preparing a compound of the formula

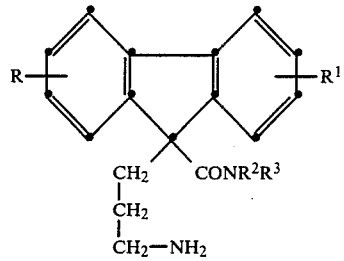

wherein R and $R^1$ independently are hydrogen, $C_1$–$C_4$ alkyl, fluoro or chloro; and $R^2$ and $R^3$ independently are hydrogen or $C_1$–$C_6$ alkyl, involving catalytically hydrogenating a compound of the formula

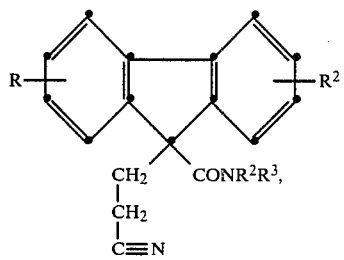

the improvement comprising conducting the reaction in the presence of an acid medium stronger than glacial acetic acid.

In a preferred embodiment of this invention the hydrogenation is carried out in the presence of trifluoroacetic acid. In another preferred embodiment the hydrogenation is carried out in the presence of a mineral acid such as hydrochloric acid.

DETAILED DESCRIPTION OF THE INVENTION

The process provided by this invention is carried out by catalytically hydrogenating a 9-carbamoyl-9-(2-cyanoethyl)fluorene in an acid medium stronger than glacial acetic acid. As pointed out in U.S. Pat. No. 4,282,170, the hydrogenation of the cyano group of a cyanoethylfluorene can be accomplished employing any of the common hydrogenation catalysts, including platinum, palladium, nickel, rhodium and ruthenium. The process generally will be carried out under a hydrogen pressure of about 1 to about 4 atmospheres, and typically at a temperature of about 20° to about 70° C.

The hydrogenation process of this invention can be carried out in essentially any organic solvent; all that is required is that about one molar equivalent or more of an acid stronger than glacial acetic acid be present in the reaction mixture. Organic solvents that can be employed include alcohols, ethers, aromatics, amides, as well as organic or inorganic acids and mixtures of acids. For example, the process is conveniently carried out in an alcohol such as methanol or ethanol together with at least about one molar quantity, relative to the cyanoethylfluorene to be reduced, of a strong acid such as 12N hydrochloric acid or the like.

Any acid that is stronger than acetic acid can be employed in the process of this invention. Such acids include those having a $pK_a$ less than about 4.75, the $pK_a$ of glacial acetic acid at 25° C. Exemplary of the strong acids that can be employed in the present process include benzosulfonic acid, any of the aminobenzosulfonic acids, ortho or meta-bromobenzoic acid, trichloroacetic acid, the chlorobenzoic acids, 2-chlorophenoxyacetic acid, 3-chlorophenoxyacetic acid, dimethylmalonic acid, dinicotinic acid, diphenylacetic acid, fluorobenzoic acid, formic acid, fluoroacetic acid, glycolic acid, hippuric acid, 2-hydroxybenzoic acid, 2-iodobenzoic acid, itacomic acid, lutidinic acid, maleic acid, malonic acid, mesaconic acid, methylmalonic acid, naphthalenesulfonic acid, α-naphthoic acid, oxalic acid, o-phthalic acid, quinolinic acid, sulfanilic acid, α-tartaric acid, trichloroacetic acid, trifluoroacetic acid, 2,4,6-trihydroxybenzoic acid, and similar strong organic acid. Inorganic acids can also be employed and exemplary of such acids are arsenic acid, chromic acid, hydrofluoric acid, hydrochloric acid, iodic acid, nitrous acid, periodic acid, phosphoric acid, pyrophosphoric acid, selenic acid, sulfuric acid, and related strong inorganic acids.

While the mechanism of the present process is not completely understood, it is believed that the strong acid required to be employed according to the invention reacts with the primary amino group of the 9-(3-aminopropyl)fluorene as it is formed to produce an acid addition salt. Once the primary amino group is protonated as an acid addition salt, it is unavailable for reaction with other reaction intermediates to produce the dimer and trimer by-products.

The hydrogenation process of this invention generally is substantially complete within about two to about twenty-four hours when carried out at about ambient temperature and under a hydrogen pressure of about 1 to about 4 atmospheres. The 9-carbamoyl-9-(3-aminopropyl)fluorene that is produced by the process is readily isolated by established procedures if desired. For example, the reaction mixture can be filtered to remove the hydrogenation catalyst, and the reaction solvent can be removed from the filtrate, for instance by evaporation under reduced pressure. The aminopropylfluorene product can be isolated and crystallized as an acid addition salt, or if desired the salt can be neutralized by reaction with a base such as sodium hydroxide or ammonium hydroxide to provide the desired primary amine.

In a preferred embodiment of the invention the 9-carbamoyl-9-(3-aminopropyl)fluorene is not isolated, but rather is reacted further in situ to produce an N-alkyl derivative such as 9-carbamoyl-9-(3-isopropylaminopropyl)fluorene. Such alkylation is best accomplished by first neutralizing any excess acid, for instance by addition of a base such as sodium bicarbonate, and then simply adding an aldehyde or a ketone to the hydrogenation reaction mixture and subjecting the mixture to further hydrogenation. The aldehyde or ketone reacts with the primary amino group of the 9-carbamoyl-9-(3-aminopropyl)fluorene to produce the corresponding Schiff base, which upon further hydrogenation is reduced to the desired N-alkyl derivative. For example, 9-carbamoyl-9-(2-cyanoethyl)fluorene can be hydrogenated according to this invention by reaction with hydrogen gas in the presence of a catalyst such as platinum oxide and a strong acid such as trichloroacetic acid to produce, substantially free of dimer or trimer by-products, 9-carbamoyl-9-(3-aminopropyl)fluorene. The reaction mixture is neutralized by addition of a base, for example about one molar quantity or an excess of sodium hydroxide or the like. A ketone such as acetone can be added to the neutralized reaction mixture and the mixture can be further hydrogenated to provide 9-carbamoyl-9-(3-isopropylaminopropyl)fluorene. The product thus produced is substantially free of undesired by-products and can be isolated and purified by routine procedures.

The process improvement provided by this invention is further illustrated by the following detailed examples. The examples are not intended to limit the invention in any respect and should not be so construed.

EXAMPLE 1

A mixture of 100 g of 9-carbamoyl-9-(2-cyanoethyl)fluorene and 20 g of 5% palladium on charcoal in 560 ml of tetrahydrofuran and 50 ml of water was stirred at 100° C. for twenty-four hours under 1000 psi of hydrogen. The reaction mixture was filtered and the filtrate was concentrated to dryness to provide 93.5 g of a white solid identified as primarily dimer and trimer product. The solid was suspended in 500 ml of acetone and the mixture was stirred at 25° C. for one hour and then filtered to give 34 g of a white solid. The filtrate was concentrated to give 50 g of a white solid. The white solids were combined and triturated in 675 ml of hot tetrahydrofuran. The mixture was filtered and the solvent was removed from the filtrate to give 69.9 g of a white solid melting at 162.5°–165° C. The solid was chromatographed twice over silica gel, eluting with tetrahydrofuran, to give a substantially pure sample of

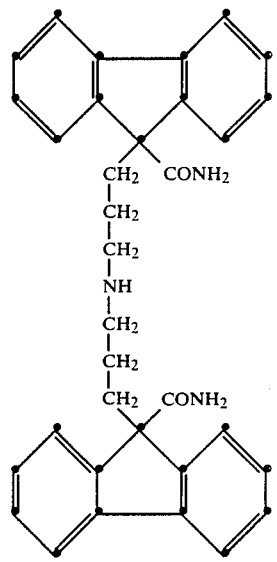

Analysis calculated for $C_{34}H_{33}N_3O_2$: Theory: C, 79.19; H, 6.45; N, 8.15; Found: C, 77.17; H, 6.33; N, 7.39.

Eight grams of the above dimer were added to 200 ml of ethyl acetate and 150 ml of methanol containing 1.8 g of maleic acid. The reaction mixture was heated at 100° C. for one hour and then cooled. The crystalline precipitate was filtered and air dried to give 9.8 g of 9,9'-(iminodi-3,1-propanediyl)bis[9H-fluorene-9-carboxamide](Z)-2-butene-dioate (1:1) having the formula

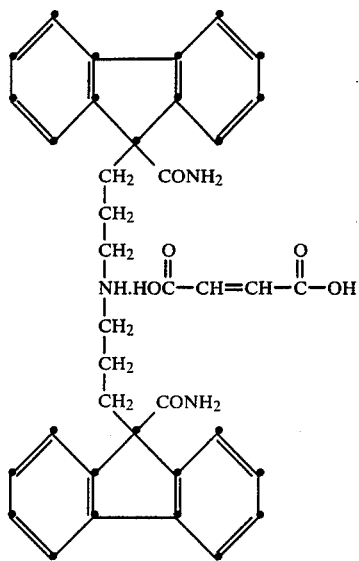

M.P. 185°–187° C.

Analysis calculated for $C_{38}H_{37}N_3O_6$: Theory: C, 72.25; H, 5.90; N, 6.65; Found: C, 71.97; H, 6.00; N, 6.40.

EXAMPLE 2

A mixture of 15.02 g (57.2 mM) of 9-carbamoyl-9-(2-cyanoethyl)fluorene and 4.0 g platinum oxide in 200 ml of glacial acetic acid was shaken at 25° C. under a hydrogen atmosphere (4 atm) for three hours. The reaction mixture was diluted by addition of 5.0 g (86 mM) of acetone, and hydrogenation was continued for an additional seventeen hours. The reaction mixture was filtered and the filtrate was concentrated to dryness by evaporation of the solvents under reduced pressure to give 32.0 g of a brown viscous oil. The oil was added to 200 ml of ethyl acetate and 200 ml of ice water, and this mixture was diluted by addition of 400 ml of 6N hydrochloric acid. The aqueous acid layer was separated, made alkaline by addition of 110 ml of 50% aqueous sodium hydroxide. The aqueous alkaline solution was extracted several times with diethyl ether, and the ethereal extracts were combined, washed with water, dried and the solvent was removed by evaporation to give 13.4 g (76.1% yield) of product. The product was shown by high performance liquid chromatography to be comprised of 83.4% 9-carbamoyl-9-(3-isopropylaminopropyl)fluorene and 8.2% of dimer, N,N-bis-[3-(9-carbamoylfluoren-9-yl)propyl]amine, identical to that prepared and characterized in Example 1.

EXAMPLE 3

A solution of 10.1 g (38 mM) of 9-carbamoyl-9-(2-cyanoethyl)fluorene in 190 ml of glacial acetic acid and 3.3 ml of 12N hydrochloric acid containing 2.0 g of platinum oxide was shaken for six hours at 25° C. in a Parr hydrogenator under 4 atm. of hydrogen. The reaction mixture was neutralized by addition of 3.1 g (38 mM) of sodium acetate, followed by addition of 8.34 ml of acetone. The reaction mixture was shaken for an additional sixteen hours under 4 atm. of hydrogen. An additional 2.75 ml of acetone were added to the reaction mixture and it was shaken under hydrogen for another two hours. The reaction mixture was filtered and the filtrate was concentrated to 36.0 g of a viscous liquid. The liquid was dissolved in 200 ml of water and the aqueous solution was washed with diethyl ether and then made alkaline by addition of 50% (w/v) aqueous sodium hydroxide. The alkaline mixture was extracted several times with diethyl ether and the ethereal extracts were combined, washed with water and dried. Removal of the solvent by evaporation under reduced pressure afforded 9.6 g (82% yield) of a tan solid.

A solution of 9.4 g of the tan solid in 110 ml of acetone was cooled to 0°–5° C. and diluted by addition of 3 ml of 12N hydrochloric acid. The reaction mixture was stirred at 0°–5° C. for one hour, whereupon the white precipitate that had formed was collected by filtration and air dried to give 7.6 g of a product melting at 191°–194° C.

The product thus obtained was crystallized from 90 ml of hot (80° C.) isopropanol to give 4.8 g of 9-carbamoyl-9-(3-isopropylaminopropyl)fluorene hydrochloride melting at 205°–207° C. High performance liquid chromatography demonstrated the product to be at least 97.6% pure, with less than 1% of dimer being present.

Analysis calculated for $C_{20}H_{25}ClN_2O$: Theory: C, 69.65; H, 7.31; N, 8.12; Found: C, 69.84; H, 7.47; N, 7.92.

NMR (DMSO$_{d6}$): δ 1.1 (d, 6H); 2.1–3.3 (m, 6H); 3.42 (s, 1H); 6.3 (s, 1H); 7.0 (s, 1H); 7.4–8.2 (m, 8H); 8.6–9.0 (broad s, 2H).

EXAMPLE 4

A solution of 10.1 g of 9-carbamoyl-9-(2-cyanoethyl)fluorene in 193 ml of glacial acetic acid and 8.66 g of trifluoroacetic acid containing 2.0 g of platinum oxide was shaken for six hours under 4 atm. of hydrogen in a Parr hydrogenation flask. The reaction mixture was filtered and the filtrate was concentrated to give 28.6 g of a viscous liquid. The liquid was added to 200 ml of ice water and the aqueous mixture was washed with dichloromethane. The aqueous layer was made alkaline by addition of 50% (w/v) aqueous sodium hydroxide, and the aqueous alkaline solution was extracted several times with dichloromethane. The organic extracts were combined, washed with water, dried, and the solvent was removed by evaporation under reduced pressure to give 9.9 g (97% yield) of a tan solid identified by thin layer chromatography as 9-carbamoyl-9-(3-aminopropyl)fluorene.

A solution of 9.1 g of the product from above in 190 ml of ethanol and 8.34 ml (6.66 g, 114 mM) of acetone containing 2.0 g of 5% palladium on charcoal was shaken for twenty hours at 25° C. under 4 atm of hydrogen. The reaction mixture was filtered and the filtrate was concentrated to 13.1 g of a viscous liquid. The liquid was added to 200 ml of water and 200 ml of diethyl ether. The aqueous layer was separated, made alkaline by addition of 50% sodium hydroxide, and extracted several times with diethyl ether. The ethereal extracts were combined, extracted with 300 ml of 6N hydrochloric acid and 200 ml of water. The aqueous acid extracts were combined, made alkaline, and then extracted with fresh diethyl ether. The ethereal extracts were combined, washed with water, dried and concentrated to give 9.9 g (84.6% yield) of a white solid. The solid was dissolved in 100 ml of cold (0°–5° C.) acetone and the solution was saturated with hydrogen chloride. The mixture was stirred for forty-five minutes and filtered to give 8.0 g (77.8%) of 9-carbamoyl-9-(3-isopropylaminopropyl)fluorene hydrochloride. The product was recrystallized from isopropanol to give 4.7 g (58.7% yield) of the hydrochloride salt melting at 206°–208° C.

High pressure liquid chromatography established the product to be almost 100% 9-carbamoyl-9-(3-isopropylaminopropyl)fluorene hydrochloride, with no detectible amounts of dimer or trimer.

Analysis calculated for $C_{20}H_{25}ClN_2O$: Theory: C, 69.65; H, 7.31; N, 8.12; Found: C, 69.90; H, 7.44; N, 8.03.

NMR (DMSO$_{d6}$): δ 1.1 (d, 6H); 2.1–3.4 (m, 7H); 6.22 (s, 1H); 7.0 (s, 1H) 7.4–8.2 (m, 8H); 8.5–9.1 (broad s, 2H)

EXAMPLE 5

A solution of 10.1 g (38 mM) of 9-carbamoyl-9-(2-cyanoethyl)fluorene in 190 ml of ethanol and 8.66 g (76 mM) of trifluoroacetic acid containing 2.0 g of platinum oxide was shaken for four and one-half hours at 25° C. under 4 atm. of hydrogen. The reaction mixture was then added to a mixture of 2.0 g of 5% palladium on charcoal in 20 ml of ethanol containing 8.34 ml of acetone and 6.3 g sodium acetate. This reaction mixture was shaken for twenty hours at 25° C. under 4 atm. of hydrogen. The reaction mixture was filtered and the filtrate was concentrated to give 32.2 g of a viscous oil. The oil was added to 200 ml of ice water and the aqueous mixture was made alkaline by addition of 50% (w/v) aqueous sodium hydroxide. The aqueous alkaline mixture was extracted several times with diethyl ether. The ethereal extracts were combined and extracted with 300 ml of 6N hydrochloric acid and 200 ml of water. The aqueous acid extracts were combined, made alkaline by addition of fresh sodium hydroxide, and extracted with fresh diethyl ether. The ethereal extracts were combined, washed with water, dried and concentrated to dryness to give 11.1 g (94.8% yield) of product. The product was dissolved in 80 ml of acetone and the solution was saturated with hydrogen chloride to give 10.2 g (91.8%) of white solid. The solid was crystallized from 105 ml of isopropanol to provide 6.8 g (66.5%) of 9-carbamoyl-9-(3-isopropylaminopropyl)fluorene hydrochloride. M.P. 205°–208° C. High performance liquid chromatography demonstrated that the product contained no detectable amount of dimer or trimer. Elemental analysis and NMR were consistent with those for the products of Examples 3 and 4.

We claim:

1. In a process for preparing a compound of the formula

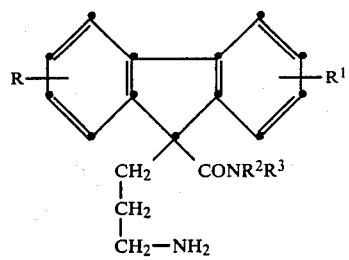

wherein:

R and $R^1$ independently are hydrogen, $C_1$–$C_4$ alkyl, fluoro or chloro; and $R^2$ and $R^3$ independently are hydrogen or $C_1$–$C_6$ alkyl;

which includes catalytically hydrogenating a compound of the formula

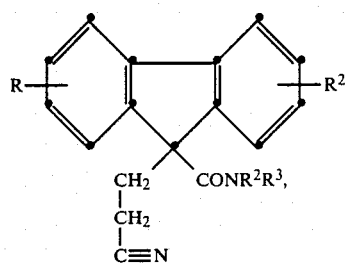

the improvement comprising conducting the reaction in the presence of an acid medium stronger than glacial acetic acid.

2. The process according to claim 1 employing trifluoroacetic acid.

3. The process according to claim 1 employing a mineral acid.

4. The process according to claim 1 wherein R and $R^1$ both are hydrogen.

5. The process according to claim 4 wherein $R^2$ and $R^3$ both are hydrogen.

6. The process according to claim 5 employing trifluoroacetic acid.

7. The process according to claim 5 employing hydrochloric acid.

* * * * *